(12) United States Patent
Tweardy

(10) Patent No.: US 6,896,678 B2
(45) Date of Patent: May 24, 2005

(54) CERAMIC-TIPPED SKULL PINS

(75) Inventor: Lisa A. G. Tweardy, Thalwil (CH)

(73) Assignee: The Jerome Group, Inc., Moorestown, NJ (US)

( * ) Notice: Subject to any disclaimer, the term of this patent is extended or adjusted under 35 U.S.C. 154(b) by 0 days.

(21) Appl. No.: 09/917,385

(22) Filed: Jul. 27, 2001

(65) Prior Publication Data

US 2002/0042618 A1 Apr. 11, 2002

Related U.S. Application Data

(60) Provisional application No. 60/238,162, filed on Oct. 5, 2000.

(51) Int. Cl.[7] ............................................... A61B 17/58
(52) U.S. Cl. ............................ 606/72; 606/75; 411/487
(58) Field of Search ................................. 411/487, 493, 411/498, 499, 904, 907, 908, 440; 52/410; 606/130, 56, 54, 72, 75, 63, 232; 602/36

(56) References Cited

U.S. PATENT DOCUMENTS

| | | | | |
|---|---|---|---|---|
| 2,672,861 A | * | 3/1954 | Jonas et al. .................... 606/63 |
| 4,018,023 A | * | 4/1977 | Anderson ..................... 52/410 |
| 4,612,930 A | * | 9/1986 | Bremer ........................ 411/386 |
| 4,858,603 A | * | 8/1989 | Clemow et al. ............... 606/72 |
| 5,042,462 A | * | 8/1991 | Bremer ........................ 602/36 |
| 5,122,132 A | * | 6/1992 | Bremer ........................ 411/386 |
| 5,494,034 A | * | 2/1996 | Schlondorff et al. .......... 378/20 |
| 5,606,832 A | * | 3/1997 | Keith et al. ................... 52/410 |
| 5,658,109 A | * | 8/1997 | Van Allman et al. ........ 411/440 |
| 5,669,912 A | * | 9/1997 | Spetzler ........................ 606/72 |
| 5,752,962 A | * | 5/1998 | D'Urso ........................ 128/857 |
| 5,769,861 A | * | 6/1998 | Vilsmeier .................... 600/426 |
| 5,868,789 A | * | 2/1999 | Huebner ...................... 606/232 |
| 5,893,369 A | * | 4/1999 | LeMole ....................... 606/184 |
| 5,961,528 A | * | 10/1999 | Birk et al. ................... 411/386 |
| 6,045,553 A | * | 4/2000 | Iversen et al. ................ 606/72 |
| 6,342,054 B1 | * | 1/2002 | Mata ............................ 606/54 |
| 6,387,129 B2 | * | 5/2002 | Rieser et al. ............ 623/13.14 |

* cited by examiner

Primary Examiner—Julian W. Woo
(74) Attorney, Agent, or Firm—Schnader Harrison Segal & Lewis LLP

(57) ABSTRACT

A skull pin including a removable tip is disclosed where the tip of the pin is manufactured from a ceramic material. Alternatively, the tip can be manufactured from other insulating, non-conducting materials. The tip may either be inserted into a bore in the center of the pin, or may be a cap placed over the pin.

15 Claims, 3 Drawing Sheets

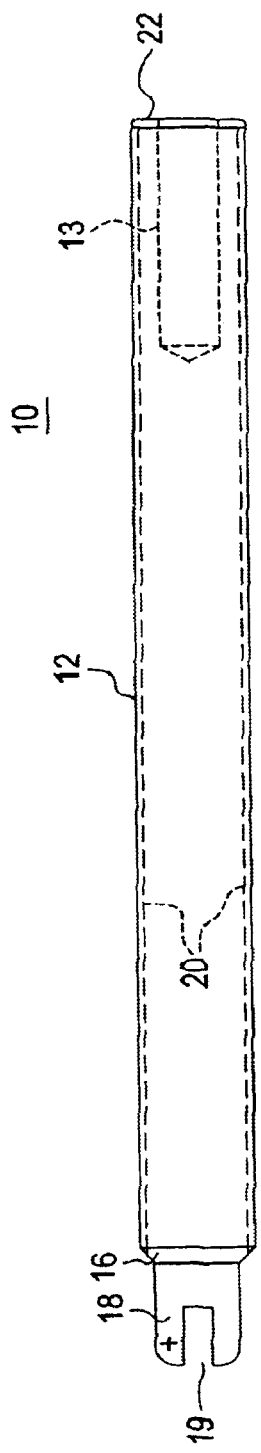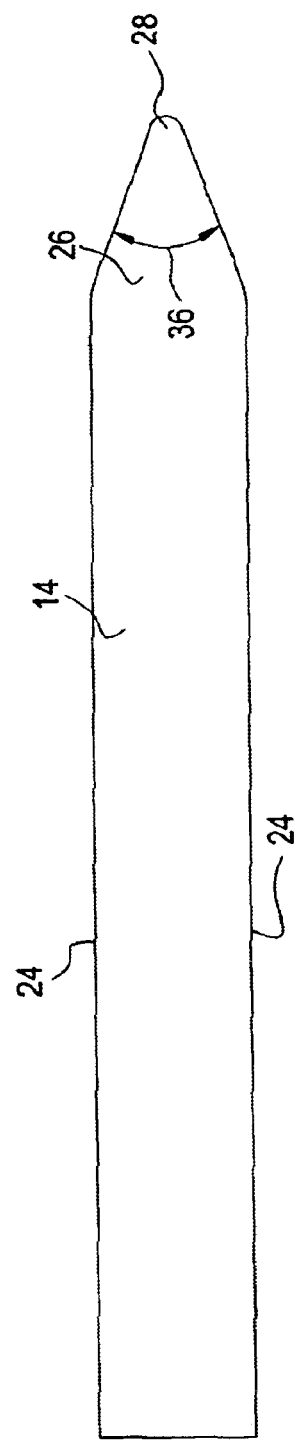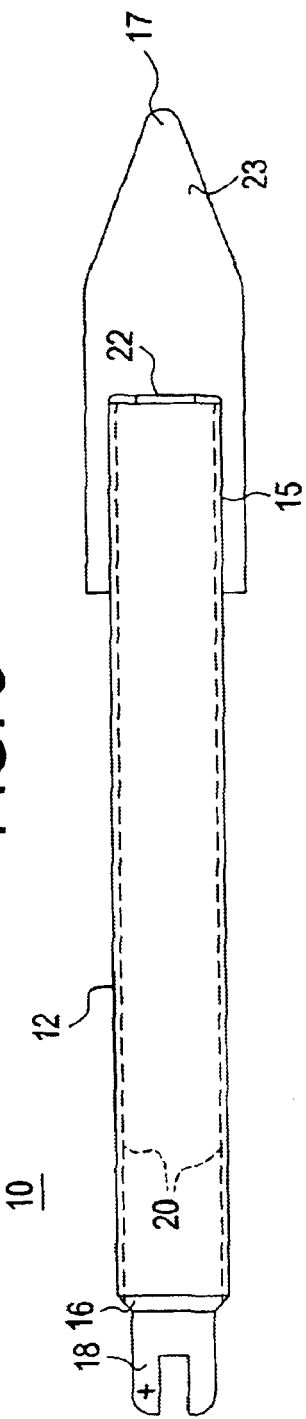

US 6,896,678 B2

CERAMIC-TIPPED SKULL PINS

CROSS REFERENCE TO RELATED APPLICATION

This application claims the benefit under Title 35 U.S.C. § 120 of U.S. Provisional Application No. 60/238,162 filed on Oct. 5, 2000.

FIELD OF INVENTION

The present invention relates to part of a medical apparatus for rigidly securing a patient's head during the treatment of fractures of the cervical spine. More specifically, it relates to skull pins which are inserted through the holes of a halo or through the holes of a tong and into the patient's skull.

DESCRIPTION OF THE PRIOR ART

When the head of a patient must be placed and held in a predetermined immobilized position with respect to the patient's body for medical treatment, a traction system may be used such as is taught in U.S. Pat. No. 5,302,170. The traction system may be a halo which rings the patient's head and is used for long-term immobilization or a traction tong which consists of two arms placed on the sides of the patient's head and is used to apply traction to the patient. Regardless of whether the physician uses a halo or a tong, skull pins are generally used which project through holes in the halo or the tong and into the patient's skull. One end of each skull pin has a pointed tip to bear into the skull bone of the patient and hold the halo or tongs rigidly to the skull. A compression force is applied to the skull pins to hold the patient's head in a fixed position.

After a halo or a tong is attached to a patient's head using skull pins, it is often necessary to perform radiographic studies of the patient's head in order to diagnose the nature of the patient's injury. A typical radiographic modality is magnetic resonance imaging, commonly known as MRI, a technique which subjects the patient to various magnetic fields.

Prior art skull pins have typically been fashioned from titanium, alloy, or stainless steal. When such skull pins are used, patients commonly complain of a sudden focal heating sensation at the skull pin contact locations. In the past, the problem was minimal. Recently, MRI machines have become increasingly powerful. The added power causes greater potential for inducing current within the conductive material and greater potential for focal heating sensation of the metal pins. The problem is becoming acute, with patients suffering severe burns from the pins. U.S. Pat. No. 5,961,528 attempted to solve this problem by manufacturing a skull pin using a metallic tip section attached to non-metallic insulator. The theory was that even though the metallic tip section would still contact the patient's head, the prior problems would no longer exist because the non-metallic insulator would decrease current flow through the tip during the MRI.

However, pin heating complications in patients undergoing MRI while fixated in a halo or tong still occur. The degree of complications has ranged from artifact and poor visualization in the MRI scans to evidence of burns and severe pin pain. Further, a simple insulator such as that shown in U.S. Pat. No. 5,961,528, or even the pin tip described in U.S. Pat. No. 5,122,132 to Bremer do not fully solve the problem. In both cases, the insulating material is too small, and arcing can occur between the pin body and the patient, again causing burns or a current can be induced within the metallic pin tip itself.

An advantage of the present invention is that it allows an MRI to proceed without the problems associated with the prior art skull pin designs.

BRIEF SUMMARY OF THE INVENTION

The present invention is a skull pin including a removable tip, where the tip of the pin is manufactured from a ceramic material. That is, the pin is ceramic tipped. Alternatively, the tip can be manufactured from other insulating, non-conducting materials. The tip may either be inserted into a bore in the center of the pin, or may be a cap placed over the pin.

BRIEF DESCRIPTION OF THE DRAWINGS

FIG. 1 is a partial cross-sectional view of an embodiment of a skull pin body in accordance with the present invention.

FIG. 2 is a side view of an embodiment of the pin tip manufactured in accordance with the present invention.

FIG. 3 is a partial cross-sectional view of another embodiment of a skull pin body where the pin tip covers the distal end of the pin body.

DETAILED DESCRIPTION OF THE INVENTION

Figure 4:
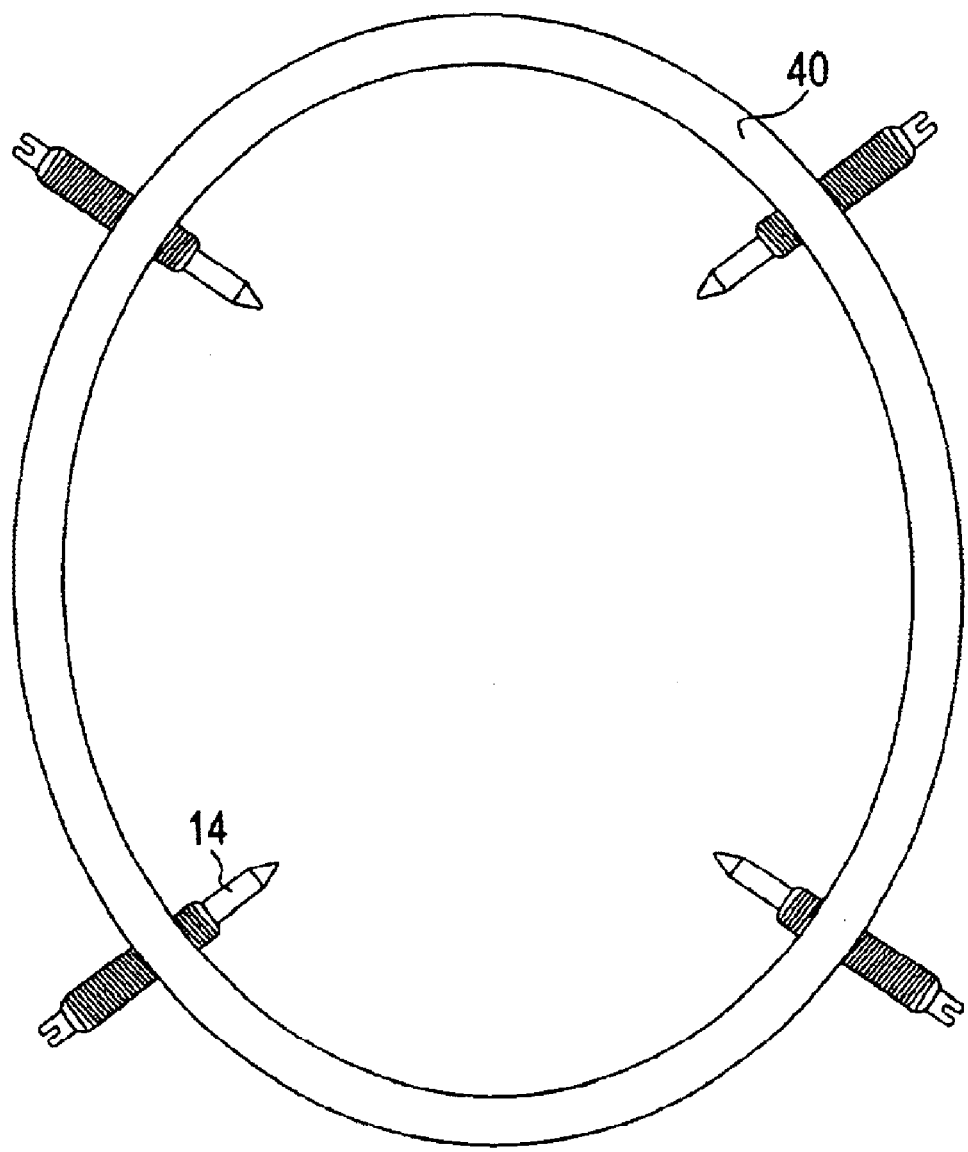
FIG. 4 depicts a halo according to an illustrative embodiment of the invention.

In conducting an investigation into the causes of the problems outlined above, it was discovered that the use of advanced magnetic resonance imaging techniques, necessary in high-resolution scans of the brain and/or spinal cord, produced imaging interference associated with, but not limited to, electrical current induction when industry standard pins were applied. The hypothesis is based on Faraday's law and Ohm's law. In accordance with Ohm's Law, $C=E/R$, where C=current, E=induced voltage, and R=resistance, a perfect insulator would result in the current equaling zero. Using Ohm's Law, it has been determined that voltages greater than four volts produces perceptible heating and pain. Therefore, the solution created by the present invention consists of creating a path of most resistance by insulating the patient from any induced current, any induced voltage, and, therefore, from any heating and pain caused by the skull pins. The purpose of the insulation is to block current which can create Joule heating in accordance with Faraday's Law in the area of contact with the skull pin. By blocking Joule heating in the area of skin contact with the skull pin, no perceptible heating occurs.

Referring now to FIG. 1, one embodiment of the present invention is shown as skull pin 10 which comprises a pin body 12 and pin tip 14, shown in FIG. 2. Pin body 12 is generally cylindrical. Proximal end 22 of pin body 12 includes a bore 13. Distal end 16 of pin body 12 includes a head 18 which has a slot 19 or is otherwise equipped for turning and tightening skull pin 10 through threaded holes in a halo or tong. Pin body 12 includes threads 20 along its exterior so that it can be screwed into such threaded holes in a halo or a tong. Proximal end 22 of pin body 12 has a generally cylindrical bore 13 which is open and can receive pin tip 14. Pin body 12 may be made of any suitably strong material such as titanium. The material for pin body 12 should be suitable for use in an MRI machine (i.e., it should be non-ferrous, non-magnetic). Pin tip 14 is also generally cylindrical. Specifically, the shape of pin tip 14 and bore 13 must match at least insofar as pin tip 14 can fit snugly in bore 13. Pin tip 14 forms the tip of skull pin 10 and is the part of skull pin 10 that comes in contact with the patient's skull. Its diameter is small enough to fit inside bore 13 in pin body 12, but large enough to form a tight fit inside bore 13. Pin tip 14 can be smooth, or can be threaded or splined if desired. Pin tip 14 is made from a strong, non-conducting material such as a ceramic.

In one embodiment of pin tip 14, the pin tip is manufactured from Prozyr, a tetragonal zirconia manufactured from very fine and pure yttria stabilized zirconium oxide powder. Prozyr is a trade mark of, and is available from, Norton Desmarquest of Connecticut. Such material provides wear resistance and strength and can safely withstand up to 200 pounds of axial load, 200 pounds of shear forces, and 200 pounds of traction at the sizes used in the present invention. This material is also biocompatible and electronically inert. That is, it decreases the likelihood of infection at the point of entry into the patient's skull and does not transmit induced current, voltage, or heat to the patient's skull. As will be recognized by those skilled in the art, other ceramic materials having the same or similar characteristics can be used in place of Prozyr. Further, the entire skull pin 10 can be manufactured from a sufficiently strong non-conducting ceramicor even another suitable material which is electronically inert and non-conductive. For example, a plastic material can be used if it is strong enough to withstand up to the 200 pound axial, shear, and traction loads.

By using a ceramic tipped skull pin, there is an insulating ceramic between the patient's skull and the halo or tong. There is no metal contacting the skull.

FIG. 2 shows the shape of a complete pin tip 14. Pin tip 14 is a cylinder with straight sides 24 for most of its length. Toward the proximal end of the pin is a tapered portion 26. As used herein, "proximal" refers to an end nearer the patient when the pin is in place, and "distal" refers to an end farther from the patient. The point 28 of the tapered portion 26 is rounded, rather than coming to a sharp point. Point 28 is the part of pin tip 14 which actually comes into contact with the patient's skull. The tip is rounded for strength and to prevent the ceramic material from breaking under high traction pressure and other stress loads, as could occur with a sharply pointed tip.

In a preferred embodiment, skull pin 10 is designed to be used with the industry standard halo or the industry standard tong and their industry standard skull pin or tong pin dimensions. The diameter of the embodiment of the skull pin 10 conforming to industry standard dimensions preferably has a pin tip 14 with a diameter of 3.2300 mm±0.05 mm (0.127 inch). The total length of pin tip 14 is preferably 30.0800 mm±1 mm (1.18425 inch). Of course, this length may vary somewhat, but is preferably between 10 and 50 mm, more preferably between 15 and 50 mm, and more preferably between 20 and 35 mm. Most preferably, pin tip 14 is about 25 mm in length.

The angle 36 between the tapered portions 26 is about 40° but can be in the range of about 30° to 50°. The angle must be chosen so that the angle is sufficiently small to be capable of holding the pin in place in the bone of the patient's skull, while not so small that the pin will break easily. The radius of rounded end 28 is between 0.025 and 0.075 mm, preferably between 0.04 and 0.06, and more preferably about 0.05 mm. The radius is chosen so that pin tip 14 does not slip out of the patient's bone, but yet the tip is structurally strong and stable. The radius can be made larger or smaller than 0.05 mm, providing it meets these conditions.

The length of the tapered portion 26 of the ceramic pin, including rounded point 28, is preferably between 2.5–6.0 mm, more preferably 3.5–5.0 mm, and most preferably between 4.0 and 4.5 mm. The overall length of pin tip 14 is between 10 and 50 mm, preferably between 15 and 50 mm, more preferably between 20 and 35 mm, and most preferably about 25 mm. The bore 13 in pin body 12 can be any suitable length. However, bore 13 should be sized according to the size of pin tip 14. Specifically, between about 10 mm and about 30 mm of pin tip 14 should protrude from pin body 12. Preferably, about 15 mm to about 25 mm, more preferably about 15 mm to about 20 mm of pin tip 14 should protrude from pin body 12. This allows up to 10 mm of pin tip 14 to be within the skin of a patient while still allowing about 10 mm between the patient's skin and metal pin body 12. The pin tip 14 and bore 13 are preferably designed to allow at least 7.5 mm, more preferably at least 10 mm, and most preferably at least 12 mm between the patient's skin and pin body 12 to avoid arcing of electrical energy from pin body 12 to the skin of the patient.

Figure 5:
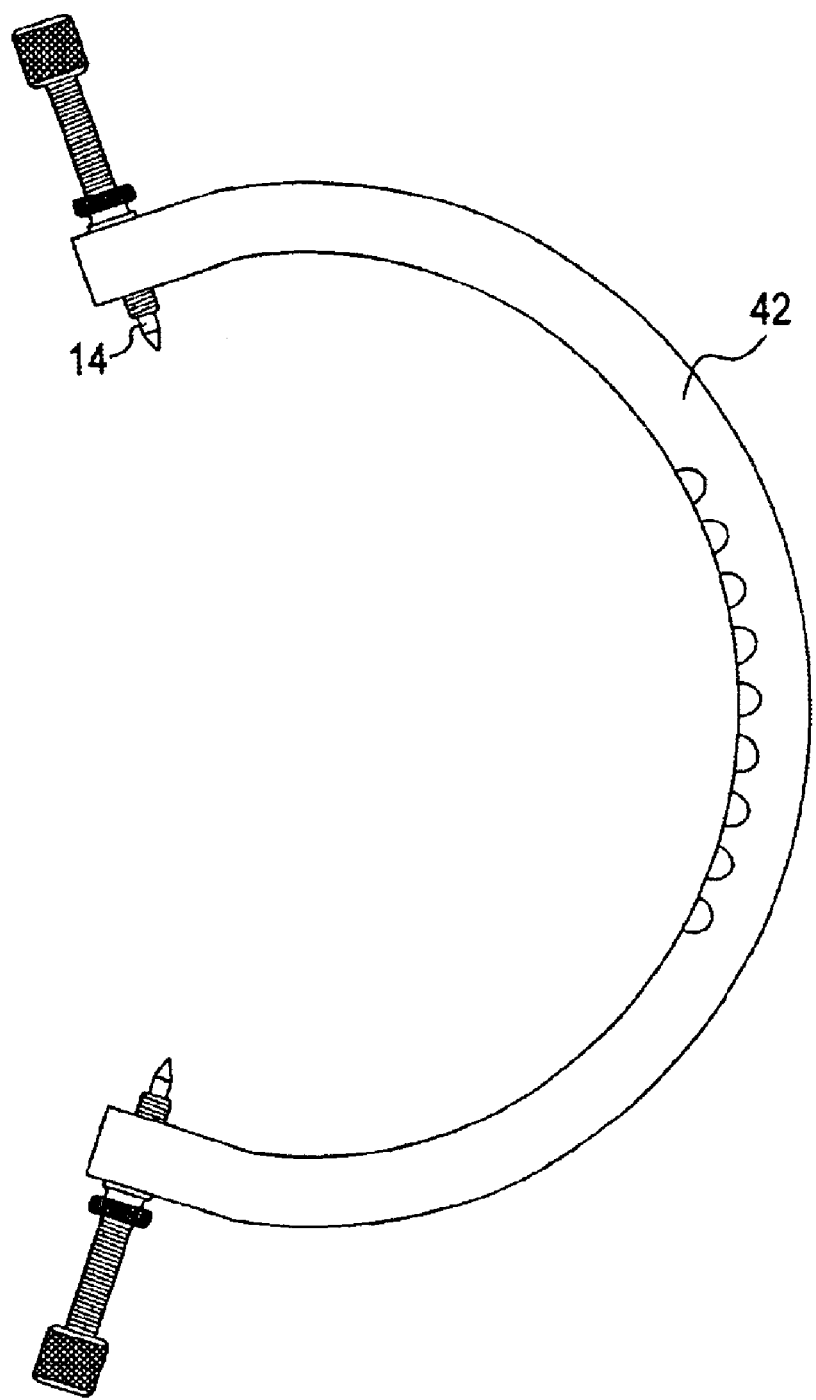
FIG. 5 depicts tongs according to an illustrative embodiment of the invention.

The insulating skull pins of the present invention can be sold individually, to retrofit older halos or tongs, or may be sold as part of a kit, along with tongs or a halo, with or without a superstructure and vest. An illustrative halo 40 and tongs 42 are depicted in FIGS. 4 and 5, respectively.

Another embodiment of the ceramic tip of the present invention is shown in FIG. 3. In that embodiment, the pin body 12 is not bored at proximal end 22. Instead, the pin tip 23 has a bore 15 to enable it to fit over the pin body. In this embodiment, the pin tip 23 would still comprise a ceramic tip manufactured from the same materials discussed above. However, the overall length of the tip could be reduced considerably. It is most desirable to leave at least about 7.5 mm, preferably at least about 10 mm, and most preferably at least about 12 mm between the skin of the patient and the exposed metal of the pin body. With ceramic cap-type pin tip 23, the pin tip need only be a total length comparable to the exposed portion of insert specified above. That is it is at least 7.5 mm, preferably at least 10 mm, more preferably at least 12 mm. These lengths are not ranges since pin tip 23 can be made longer with little fear of breakage since it gains strength from the metal pin body core. The tip 17 of the cap should be as described above with respect to pin tip 23. That is, pin tip 23 should have a proximal end which comes to a rounded tip 17, which slopes back to the body of pin tip 23 at an angle of between 30° and 50°, preferably about 40°. The radius of the rounded tip 17 of pin tip 23 is between 0.025 and 0.075 mm, preferably between 0.04 and 0.06 mm and more preferably about, 0.05 mm.

It is understood that various other modifications and uses of the embodiments of the present invention will be apparent to those skilled in the art without departing from the spirit and scope of this invention. Accordingly, it is not intended that the scope of the claims appended hereto be limited to the description as set forth therein, but rather that the claims be construed as encompassing all the features and uses of patentable novelty that reside in the present invention, including all features that would be treated as equivalents thereof by those skilled in the art to which this invention pertains. For example, it is contemplated that the skull pins could be used for fixation of the wrist or other body parts.

I claim:

1. A skull pin comprising:

a pin body; and a pin tip formed from an insulating material, protruding from a proximal end of said pin body; wherein the protruding portion of said pin tip consists of a straight-sided portion and a tapered portion with a rounded tip, the curvature of which has a spherical radius in the range of 0.025 to 0.075 mm.

2. The skull pin of claim 1, wherein said insulating material is a ceramic material.

3. The skull pin of claim 1, wherein said insulating material is an electrical insulator.

4. The skull pin of claim 1, wherein said pin body includes a bore for receiving said pin tip.

5. The skull pin of claim 1, wherein said pin tip includes a bore for receiving said pin body.

6. The skull pin of claim 1, wherein the tapered portion has an angle between 30° and 50°.

7. The pin of claim 1 wherein said straight-sided portion is cylindrical.

8. A kit comprising:
  a halo; and
  a skull pin, wherein said skull pin comprises
  a pin body, and
  an insert formed from an insulating material, protruding from a distal end of said pin body wherein the protruding portion of said insert consists of a straight-sided portion and a tapered portion with a rounded tip, the curvature of which has a spherical radius in the range of 0.025 to 0.075 mm.

9. The kit of claim 8 wherein said insulating material is a ceramic.

10. The kit of claim 8 wherein said straight-sided portion is cylindrical.

11. The kit of claim 8 wherein the tapered portion has an angle between 30° and 50°.

12. A kit comprising:
  skull tongs; and
  a skull pin, wherein said skull pin comprises
  a pin body, and
  an insert formed from an insulating material, protruding from a distal end of said pin body wherein the protruding portion of said insert consists of a straight-sided portion and a tapered portion with a rounded tip the curvature of which has a spherical radius in the range of 0.025 to 0.075 mm.

13. The kit of claim 12 wherein said insulating material is a ceramic.

14. The kit of claim 12 wherein said straight-sided portion is cylindrical.

15. The kit of claim 12 wherein the tapered portion has an angle between 30° and 50°.

* * * * *